United States Patent
Emeis et al.

(10) Patent No.: US 7,749,513 B2
(45) Date of Patent: Jul. 6, 2010

(54) METHODS OF USING A CHOLESTEROL-LOWERING PREPARATION, FOOD SUPPLEMENT AND FOODSTUFF

(75) Inventors: Josephus Jan Emeis, Amsterdam (NL); Christophe Lasseur, Wassenaar (NL)

(73) Assignee: Nederlandse Organisatie voor Toegepast-Natuurwetenschappelijk Onderzoek TNO, Delft (NL)

( * ) Notice: Subject to any disclaimer, the term of this patent is extended or adjusted under 35 U.S.C. 154(b) by 0 days.

(21) Appl. No.: 12/368,583

(22) Filed: Feb. 10, 2009

(65) Prior Publication Data

US 2009/0148412 A1 Jun. 11, 2009

Related U.S. Application Data

(62) Division of application No. 10/538,531, filed as application No. PCT/NL03/00884 on Dec. 12, 2003, now abandoned.

(30) Foreign Application Priority Data

Dec. 12, 2002 (NL) .................................. 1022153

(51) Int. Cl.
*A61K 39/02* (2006.01)
*A61K 47/00* (2006.01)
*A61K 9/28* (2006.01)
*A61K 9/48* (2006.01)
*A61K 9/20* (2006.01)
*A61K 39/38* (2006.01)
*A01N 63/02* (2006.01)

(52) U.S. Cl. .................... 424/234.1; 424/439; 424/441; 424/451; 424/464; 424/184.1; 424/780; 435/243; 435/252.1

(58) Field of Classification Search .................. None
See application file for complete search history.

(56) References Cited

U.S. PATENT DOCUMENTS 6,916,478 B2   7/2005   Kadurugamuwa et al.

FOREIGN PATENT DOCUMENTS

| CN | 1172653 | 2/1998 |
|----|---------|--------|
| CN | 1274584 | 11/2000 |
| JP | 08 205819 | 8/1996 |

OTHER PUBLICATIONS

English Abstract and Translation of Mengjun et al CN 1274584 A Nov. 29, 2000—19 pages.*
Pietsch et al (Arch Microbiol (1990) 154:433-437).*
Zurdo et al., "Dimeric carotenoid interaction in the light-harvesting antenna of purple photogrophic bacteria", Biochem. J. (1991), vol. 274, pp. 881-884.
Schmidt-Dannert, "Engineering novel carotenoids in microorganisms", Current Opinion in Biotechnology (2000), vol. 11, pp. 255-261.
Fung et al., "Practical Application of Bacterial Membrane Fraction", Journal of Rapid Methods and Automation in Microbiology (1997), vol. 5, p. x.
ATCC® Bacteria and Bacteriophages catalog (1996), p. 108.
Pfennig et al., "A New Isolate of the *Rhodospirillum fulvum* Group and its Photosynthetic Pigments", Archiv fur Mikrobiologie (1965), vol. 51, pp. 258-266.
Imhoff et al., "Reclassification of species of the spiral-shaped phototrophic purple non-sulfur bacteria . . . ", International Journal of Systematic Bacteriology (1998), vol. 48, pp. 793-798.

* cited by examiner

*Primary Examiner*—Robert Mondesi
*Assistant Examiner*—Oluwatosin Ogunbiyi
(74) *Attorney, Agent, or Firm*—Weingarten, Schurgin, Gagnebin & Lebovici LLP

(57) ABSTRACT

The present invention relates to cholesterol-lowering preparations, in particular to a bacterial preparation for use as a medicament for lowering of the blood cholesterol level. The present invention provides inter alia a preparation of *Rhodospirillum* spp. and/or *Phaeospirillum* with cholesterol-lowering effects, food supplements and foodstuffs comprising said preparation and methods for the preparation and use thereof.

10 Claims, 13 Drawing Sheets

METHODS OF USING A CHOLESTEROL-LOWERING PREPARATION, FOOD SUPPLEMENT AND FOODSTUFF

This is a divisional application of U.S. application Ser. No. 10/538,531, (abandoned), filed on Nov. 30, 2005 now abandoned as a 371 national phase filing of PCT/NL2003/000884, which was filed on Dec. 12, 2003 claiming priority to Dutch Application No. NL 1022153, filed Dec. 12, 2002. Each of the above named related applications is incorporated herein by reference.

FIELD OF THE INVENTION

The present invention relates to cholesterol-lowering preparations, in particular to a bacterial preparation for use as a medicament for lowering of the blood plasma cholesterol levels. The invention further relates to a pharmaceutical preparation, a food supplement containing this preparation, a foodstuff containing this food supplement, and to methods for their preparation.

BACKGROUND OF THE INVENTION

Cardiovascular disease is caused by a number of synergistic factors, the most important being a too high blood cholesterol level. Cholesterol is an essential building block for animal and human cells, since it is a component of cell membranes. Human cells can synthesize their own cholesterol, but cholesterol is also assimilated from food. Both processes play an important part in cholesterol metabolism.

Apart from its essential biological role as a building block for cellular membranes, cholesterol also has negative effects on human health, as a cause of cardiovascular disease (such as, for instance, myocardial infarction, stroke, and peripheral vascular disease), more specifically in relation to the occurrence of atherosclerotic lesions in the blood vessel wall. An elevated plasma cholesterol level is the most important predictive risk factor for the occurrence of cardiovascular disease and atherosclerosis.

In blood plasma, cholesterol is transported in so-called lipoproteins, which can be subdivided into a number of different classes, based on their diameter and specific density. The very-low-density lipoproteins (VLDL), the intermediate-density lipoproteins (IDL), the low-density lipoproteins (LDL), and the high-density lipoproteins (HDL) constitute the most important classes of lipoproteins.

Experimental and clinical studies have shown that the amount of cholesterol transported in the VLDL, IDL and LDL classes of lipoproteins (the so-called pro-atherogenic cholesterol) is a risk factor for the occurrence of cardiovascular disease. Cholesterol transported in HDL particles, in contrast, protects against the development of cardiovascular disease (anti-atherogenic cholesterol).

Randomized, placebo-controlled, prospective clinical studies have demonstrated that lowering plasma cholesterol has a favourable effect on the incidence of cardiovascular disease and on mortality. A prerequisite is, though, that the reduction in cholesterol should be due to a reduction in the pro-atherogenic cholesterol present in VLDL, IDL and LDL.

For the treatment and prevention of cardiovascular disease it is therefore imperative to reduce the pro-atherogenic cholesterol, and to increase, in absolute or relative proportion, the anti-atherogenic cholesterol.

A number of approaches are available to reduce plasma cholesterol. The most important are:
- to inhibit cholesterol biosynthesis;
- to increase the removal of cholesterol (and/or its metabolites, specifically bile acids) from tissues into the intestinal lumen;
- to reduce the absorption of cholesterol and bile acids from the gastrointestinal tract.

Drugs that are nowadays used to inhibit cholesterol synthesis are often inhibitors of the enzyme hydroxymethyl-glutaryl-coenzyme A reductase (HMGCoA reductase), the rate-limiting enzyme in the synthetic pathway to cholesterol. These so-called "statins" are molecules that competitively inhibit enzyme action. Examples are simvastatin ("Zocor®"), pravastatin ("Pravachol®") and atorvastatin ("Lipitor®"). Statins are generally chemically-synthesized derivatives of naturally-occurring fungal metabolites.

To increase cholesterol removal a bile acid-adsorbing resin can be used (for example cholestyramine, "Questran®"). Because of the adsorption of bile acids to the resin, their secretion in the stool is increased, and their re-absorption from the gut into the blood is reduced, resulting in a relative loss of bile acids from the body. Consequently, the liver increases the conversion of cholesterol into bile acids, resulting in a net increase in the secretion of cholesterol (metabolites) from the body. Because bile acids (by solubilizing cholesterol) are essential for the uptake of cholesterol from the lumen into the intestinal tissue, a reduction in bile acid content in the intestinal lumen will also result in a decreased cholesterol uptake.

Drugs that inhibit the active transport of cholesterol from the intestinal lumen to the blood by inhibiting cellular transport systems for cholesterol (and related sterols) in the intestinal epithelial cells are still under development. One such compound ("Ezetimibe®") has recently been registered in some countries; other related drugs are still being tested in clinical trials.

In addition to the use of drugs, the above-mentioned goals can also be reached by the use of naturally-occurring compounds, or of compounds derived from natural products (Hassel, 1998). A statin-like compound occurs spontaneously in so-called "red rice", a strain of rice carrying a mould producing lovastatin. This fungal metabolite is identical to the cholesterol-reducing medicament "Mevacor®". Another example is the occurrence, in plants, of so-called phytosterols, which competitively inhibit the intestinal uptake of cholesterol and bile acids. Phytosterols are nowadays used as cholesterol-lowering additives in the margarines "Benecol®" and "Becel Proactif®".

However, there still exists a need for cholesterol-lowering preparations, specifically for use in the food industry, and preferably aimed at human nutrition.

SUMMARY OF THE INVENTION

Surprisingly, we have found that addition of a freeze-dried preparation of *Rhodospirillum rubrum* (*R. rubrum*) to the chow of experimental animals considerably reduces the blood cholesterol level of these animals.

In a first aspect the invention now provides a preparation of *Rhodospirillum* spp. and/or *Phaeospirillum* spp. for use as a medicament. Said preparation may be any type of preparation such as a cell-free preparation comprising cellular compounds only, preferably the membrane fraction, or a preparation comprising live or dead *Rhodospirillum* spp. and/or *Phaeospirillum* spp.

In another aspect the present invention provides a pharmaceutical preparation comprising a preparation of *Rhodospirillum* spp. and/or *Phaeospirillum* spp. and one or more excipients.

In yet another aspect the present invention provides a plasma cholesterol-lowering agent comprising a preparation of *Rhodospirillum* spp. and/or *Phaeospirillum* spp.

In still another aspect the present invention relates to the use of a preparation of *Rhodospirillum* spp. and/or *Phaeospirillum* spp. for the production of a medicament for lowering plasma cholesterol.

The present invention provides in yet another aspect a food supplement with cholesterol-lowering properties, comprising a preparation of *Rhodospirillum* spp. and/or *Phaeospirillum* spp.

In another aspect the present invention provides a probiotic with cholesterol-lowering properties containing a preparation of live *Rhodospirillum* spp. and/or *Phaeospirillum* spp.

In another aspect the invention provides a foodstuff comprising a food supplement according to the invention.

In another aspect the invention provides a method for the production of a preparation of *Rhodospirillum* spp. and/or *Phaeospirillum* spp., comprising culturing one or more cells of *Rhodospirillum* spp. and/or *Phaeospirillum* spp. to a multicellular culture, harvesting said culture, and processing the cells of said culture into a preparation. A preferred embodiment of such a method comprises the processing the cells of said culture into a preparation of live *Rhodospirillum* spp. and/or *Phaeospirillum* spp.

In another aspect the invention provides a method for the production of a food supplement according to the invention, comprising making suitable for consumption a preparation of *Rhodospirillum* spp. and/or *Phaeospirillum* spp. intended for use as a medicament according to the present invention.

In another aspect the invention provides a method for the production of a foodstuff according to the invention, comprising incorporating a food supplement into a foodstuff.

DETAILED DESCRIPTION OF THE INVENTION

Figure 1:
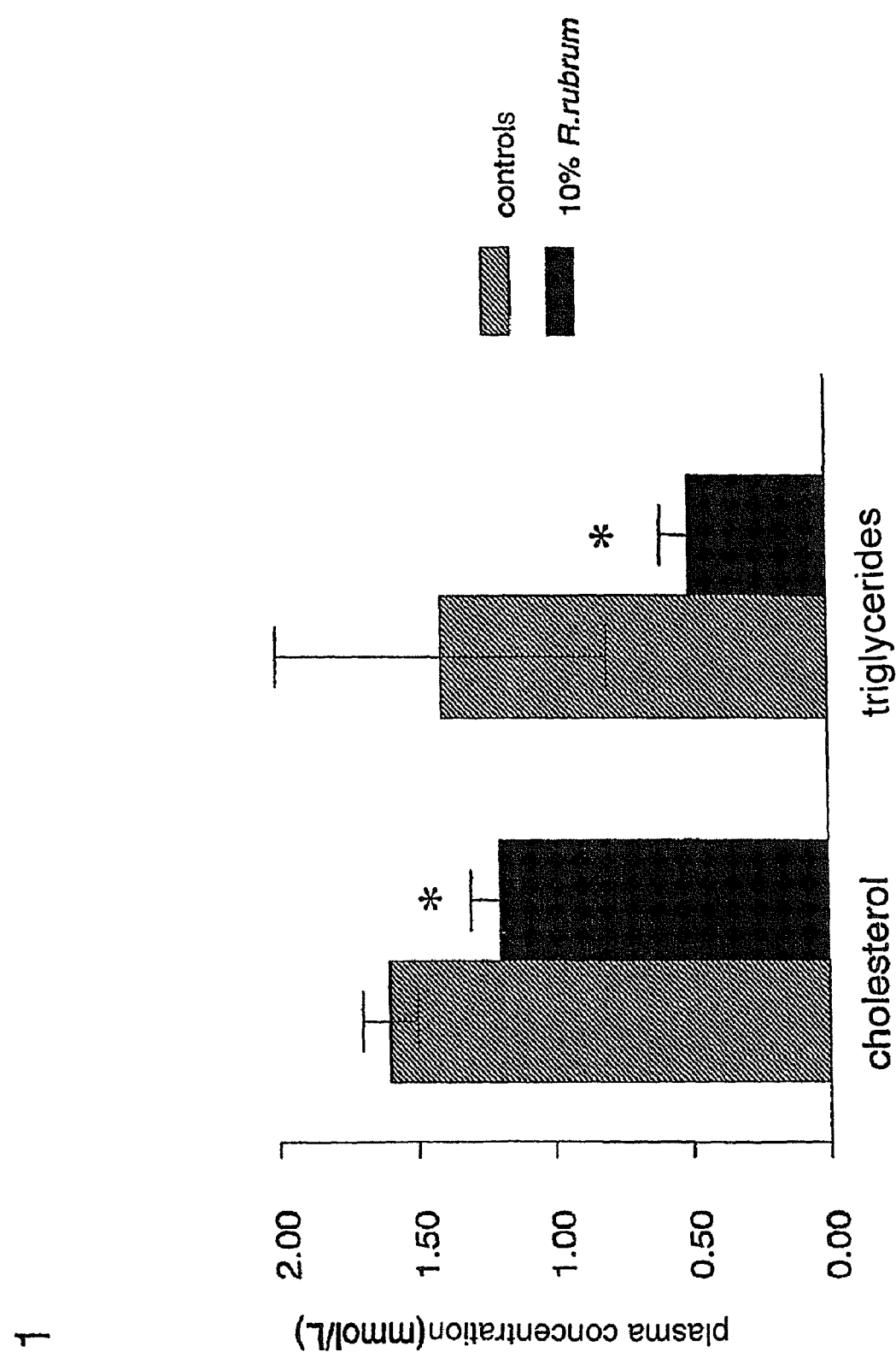
FIG. 1 shows the effect on plasma cholesterol and triglycerides in Wistar rats fed a normal chow, or a chow containing 10% (w/w) *R. rubrum*, as explained in Example 2. * means $p<0.001$ relative to controls.

*Rhodospirillum* is a genus in the family Rhodospirillaceae, a family of purple non-sulphur bacteria of the Order Rhodospirillales and the Class Alpha-proteobacteria. Rhodospirillaceae are, among other characteristics, characterized by being phototrophic, and growing both aerobically and anaerobically, using light as an energy source. To that purpose, the bacteria contain chlorophyll b. Within the genus *Rhodospirillum*, three species are distinguished, e.g. *Rhodospirillum rubrum* (Imhoff and Trüper, 1992), *Rhodospirillum centenum* and *Rhodospirillum photometricum*. Additionally, four species are not officially recognized, vz. *Rhodospirillum salexigens*, *Rhodospirillum salinarum*, *Rhodospirillum sodomense*, and *Rhodospirillum tenue*. In the genus *Phaeospirillum*, another member of the family Rhodospirillaceae, two species are included: *Phaeospirillum fulvum* and *Phaeospirillum molischianum*. (For nomenclature see Imhoff et al (1998); Euzéby (2003); and reference 1).

*Rhodospirillum rubrum* is found, among others, in natural waters, in mud, and in sewage treatment plants. The bacterium is used in sewage purification, for biomass production of animal foodstuff (for example as feed for poultry and fish), and as a fertilizer. Biomass of phototrophic bacteria is considered an excellent raw material for animal feed because of its high content of vitamins and amino acids.

The use of *Rhodospirillum rubrum* as animal feed has been practiced for some time (Imhoff and Trüper, 1992). The present inventors, however, surprisingly found that *R. rubrum* may importantly contribute to the prevention of cardiovascular disease by lowering the cholesterol level in blood plasma and/or blood serum (blood).

A cholesterol-lowering property is herein defined as the capability of a composition, a preparation, a food supplement or a foodstuff, when administered to the body of a subject in the appropriate manner, to lower the cholesterol level of the blood of said subject. Methods for measuring the level of cholesterol in blood are known to the skilled person.

A preparation of *Rhodospirillum* spp. and/or *Phaeospirillum* spp. is herein defined as an amount of cellular material of *Rhodospirillum* spp. and/or *Phaeospirillum* spp. which has been processed in some way. A preparation of *Rhodospirillum* spp. and/or *Phaeospirillum* spp. may, according to some embodiments of the present invention, comprise a cellular extract, or a component with cholesterol-lowering properties isolated from cells, or a concentrate of whole cells, or a concentrate of broken cell fragments. Such a preparation may preferably comprise the membrane fraction. In addition, a preparation may, according to the invention, contain freeze-dried *Rhodospirillum* spp. and/or *Phaeospirillum* spp., which cells are still largely alive and able to resume cell division under more favourable circumstances.

A preparation according to the invention may very well consist of one species from the genus *Rhodospirillum*, but mixtures of different *Rhodospirillum* spp. such as *Rhodospirillum rubrum, Rhodospirillum centenum, Rhodospirillum tenue, Rhodospirillum photometricum, Rhodospirillum salexigens, Rhodospirillum salinarum,* and/or *Rhodospirillum sodomense,* or mixtures of *Phaeospirillum* spp., such as *Phaeospirillum fulvum* and *Phaeospirillum molischianum* may also be used. Combinations of *Rhodospirillum* spp. and *Phaeospirillum* spp. are also encompassed in the present invention.

Preferably, a preparation of *Rhodospirillum* spp. and/or *Phaeospirillum* spp. comprises *Rhodospirillum rubrum* and/or *Phaeospirillum molischianum*, still more preferably the type species *Rhodospirillum rubrum* strain ATCC 11170 (strain DSM 467) or strain ATCC 25903 and/or *Phaeospirillum molischianum* strain DSM 120. (ATCC, American Type Culture Collection; DSMZ, Deutsche Sammlung von Mikroorganismen und Zellkulturen).

A preparation of *Rhodospirillum* spp. and/or *Phaeospirillum* spp., in embodiments of the present invention, may well contain 20-100% (w/w), preferably 40-100% (w/w), even more preferably 60-100% (w/w), and optimally 80-100% (w/w) of cellular material from *Rhodospirillum* spp. and/or *Phaeospirillum* spp., said cellular material preferably being the membrane fraction or live or freeze-dried whole cells. In addition, a preparation may contain other components, depending upon the way the selected preparation is to be prepared. For instance, a preparation may still contain water, or, in the case of a freeze-dried preparation, glycerol or sucrose.

In a preferred embodiment, a freeze-dried preparation of *Rhodospirillum* spp. and/or *Phaeospirillum* spp. is mixed with filling materials such as microcrystalline cellulose (MCC) or mannitol, with a binder such as hydroxypropylcellulose (HPC), and/or lubricants, such as stearic acid and/or other excipients, and pelleted as a dry powder, or prepared for application in a different way.

Such a preparation of *Rhodospirillum* spp. and/or *Phaeospirillum* spp. is very suitable for use as a medicament or pharmaceutical preparation to lower plasma cholesterol levels, preferably in human plasma. The preparation may also contain living cells of *Rhodospirillum* spp. and/or *Phaeospirillum* spp., or dead cells, or cell remnants, etc.

Alternative embodiments of a preparation according to the present invention are equally possible. For instance, a preparation can be supplied as a fluid preparation containing solid components suspended, dispersed or emulsified in a watery fluid. Such a composition can be used directly as a preparation according to the invention, or be processed into a food supplement in an alternative embodiment.

In the present invention a food supplement is defined as a formulation that may be consumed in addition to a normal diet and that contains components that do not occur in a normal diet, or that occur in low amounts or in insufficient amounts, while sufficient or increased consumption of these components is desired. Preferably, a food supplement is composed such that it is suitable for human consumption. Consequently, a food supplement as defined in the present invention should preferably have a texture, taste and smell, but also a nutritional value, that makes the supplement suitable for human consumption.

In embodiments of the present invention a food supplement with cholesterol-lowering properties comprises a preparation of *Rhodospirillum* spp. and/or *Phaeospirillum* spp.

A food supplement according to the invention may suitably contain from 0.1 to 99.9% (w/w) of a preparation of *Rhodospirillum* spp. Preferably, a food supplement contains 10% to 90% (w/w), even more preferably 30 to 75% (w/w), of a preparation of *Rhodospirillum* spp and/or *Phaeospirillum* spp.

To make a food supplement comprising a preparation of *Rhodospirillum* spp. and/or *Phaeospirillum* spp. suitable for consumption, components may be added to improve, for instance, texture, taste or smell. Consequently, a food supplement according to the invention may comprise (additional) sources of protein, carbohydrate and fat, and vitamins, minerals, electrolytes, trace elements, and other suitable components, so that the food supplement may itself be used as a nourishing food.

As a source of protein each and every protein that is suitable for use in nutritional formulations, and mixtures of these, can be used in a food supplement according to the invention. This type of proteins encompasses for instance animal proteins such as whey proteins, whey protein concentrates, whey powder, egg protein, egg albumin, casein, or milk albumin, and plant proteins such as soy protein, soy meal, or proteins from soy milk. For choosing the source of proteins to be used, the biological value of a protein may constitute an important criterion. Caseinate, including calcium caseinate, but also whey, milk albumin, egg albumin, and total egg proteins, for instance, are proteins with a very high biological value, because they contain a large proportion of essential amino acids.

Suitable carbohydrates to be used in a food supplement according to the invention might, for instance, be simple short-chain carbohydrates such as mono- and disaccharides, but also polysaccharides, or a combination of both. A carbohydrate may be selected because of its suitable organoleptic properties. A complex carbohydrate may suitably be used as a food fibre.

A food supplement according to the invention may contain, in some embodiments combinations of both simple and complex carbohydrates. As fat all edible oils and fats can be used.

Vitamins and minerals may be added, in conformity with the rules of the regulatory health authorities, and may encompass all vitamins and minerals endorsed by the above authorities, for instance vitamin A, B1, B2, B12, C, D, E, and K, and folic acid, niacin, panthotenic acid, and biotin. As minerals for instance iron, zinc, iodine, calcium, magnesium, chromium, and selenium may be added.

Electrolytes such as sodium, potassium, and chloride, and trace elements and other additives may also form part of a food supplement according to the invention. Such components are, if present, preferably used in the recommended concentrations. Additionally, a food supplement according to the invention may contain components improving its texture, colourings and flavourings, aromatic substances, spices, fillers, emulgators, stabilizing compounds, preservatives, antioxidants, fibres, and other supplements such as amino acids, choline, lecithin, fatty acids, etc. The choice of such components will depend upon formulation, design, and preferences. The amounts of such components that can be added are known to the skilled person, while the choice of the amounts to be added may be guided by considering the recommended daily amounts (RDA) for children and adults.

Emulsifiers may be added to stabilize the final product. Examples of acceptable emulsifiers are lecithin (e.g., soy or egg), and/or mono- and di-glycerides. As stabilizers, carobe, guar or carrageenan may, for instance, be used.

Preservatives may be added to increase the shelf life of the product. Preferably, preservatives such as sodium sorbate, potassium sorbate, potassium benzoate, sodium benzoate, or calcium disodium EDTA are used.

In addition to the carbohydrates mentioned above, natural or synthetic sweeteners, such as saccharides, cyclamates, aspartamine, acesulphame potassium, and/or sorbitol, may be added to the food supplement.

The amounts of food supplement to be consumed can vary in size, and are not necessarily restricted to the dosages mentioned in the dosages advised. The term "food supplement" is not meant to be restricted to a specified weight, or to a specified dose of the food supplement.

The composition of a food supplement according to the invention can in principle take any form that is suitable for human or animal consumption. In a preferred embodiment, the supplement is a dry powder that is suitable to be suspended, dispersed or emulsified in a watery fluid such as coffee, tea, broth, or fruit juice. To that end, the powder may be supplied in a dispenser.

In an alternative preferred embodiment, the supplement is formulated, starting from dry powder, as a tablet. To this end, the composition of a food supplement according to the invention can suitably be supplied with fillers such as microcrystalline cellulose (MCC) and mannitol, binders such as hydroxypropylcellulose (HPC), lubricants such as stearic acid, and other excipients.

A food supplement according to the invention may also be supplied as a fluid, in which the solid components have been suspended, dispersed or emulsified. Such a composition may be directly mixed into a foodstuff, or can for instance be extruded and formatted into granules or other forms.

In an alternative embodiment, a food supplement may be formulated in a solid form, such as a bar, a biscuit, or a roll.

A food supplement is preferably formulated for oral consumption, possibly in combination with an acceptable carrier such as a capsule, a tablet, a water-miscible powder, or another form acceptable for administration, but may also be processed into a foodstuff.

Other aspects of the present invention concern ways of producing a preparation, a food supplement, or a foodstuff according to the invention.

A method for the production of a preparation according to the invention may well involve the steps necessary for culturing cells of one or more *Rhodospirillum* spp. and/or *Phaeospirillum* spp., to harvest the said culture, and to process the cells of the said culture into a preparation.

Details of such methods are, among others, described in the examples mentioned below. The skilled person will understand that various alternative methods can be used.

During the culturing of cells of *Rhodospirillum* spp. and/or *Phaeospirillum* spp. anaerobic and phototrophic conditions are applied. As a carbon source, various organic nutrients can be used. Very suitable culture media and growth conditions for cells of *Rhodospirillum* spp. and/or *Phaeospirillum* spp. are for example "Segers and Verstraete medium" (Segers and Verstraete, 1983), using lactic acid (about 2.7 gram/L) as a carbon source, at a pH of about 6.8-6.9, and at a temperature of 25-37° C., preferably adapted to the specific requirements of the micro-organism involved, at constant light intensity from for instance strip lighting (light intensity 300 μM quanta·m$^{-2}$·s$^{-1}$) and anaerobically. Other media suitable for culturing *Rhodospirillum* spp. and/or *Phaeospirillum* spp. are for example "modified Rhodospirillaceae medium" (DSMZ medium #27, DMSZ GmbH, Braunschweig, Germany), or Cens medium (DSMZ medium #748). The cells are suitable to be cultured to a density of 0.01-50 mg/mL, preferably 1-5 mg wet weight/mL.

Cells may equally be grown anaerobically at 30° C. in 1 liter flasks containing a medium constituted out of 3.1 ml/160% DL-lactate solution, 3 g/l bacteriological peptone and 3 g/l yeast extract in tap water, the pH of the medium being 6.8, and illuminated with an average photon radiation strength of 50 μM quanta·m$^{-2}$·s$^{-1}$, using 3 Tungsten lamps of 40 W. After 3 days of growth, the optical density at 660 nm amounted 3.5 (1.2 g/kg dry weight).

Once the cells have reached a suitable cell density, they can be processed into a preparation according to the invention using separation from the growth medium or harvesting by, for instance, centrifugation or filtration. The concentrated cell mass can then be used, either directly or after further processing, as a preparation according to the invention.

Further steps in the processing of cell material of *Rhodospirillum* spp. and/or *Phaeospirillum* spp. to obtain a usable preparation could involve, for example, a washing step, but might also involve further processing of the cells by extraction, or freeze-drying.

A further step in the processing of cell material of *Rhodospirillum* spp. and/or *Phaeospirillum* spp. to obtain a usable preparation could involve the sonication of cells, followed by the separation of membranous material from cytoplasmatic material by centrifugation, followed by a further washing and recentrifugation step. A food supplement according to the invention may suitably be used to reduce intestinal cholesterol absorption, thus reducing the cholesterol level of blood plasma.

Another embodiment of the invention involves the application of a food supplement in a foodstuff with cholesterol-lowering properties.

A method to prepare a cholesterol-lowering foodstuff involves the production of a foodstuff incorporating a food supplement. Such a method might involve a step in which a foodstuff is first prepared in the normal way, followed by the addition of a preparation of *Rhodospirillum* spp. and/or *Phaeospirillum* spp. to the prepared foodstuff. Also, it is possible to add a preparation of *Rhodospirillum* spp. and/or *Phaeospirillum* spp. to the foodstuff during its production.

A foodstuff with cholesterol-lowering properties according to the invention contains characteristically 0.1 to 20% (w/w), preferably 1 to 10% (w/w), of the food supplement described above.

The present invention involves finally a preparation of *Rhodospirillum* spp. and/or *Phaeospirillum* spp. to be used in a medicament to lower the cholesterol level of blood plasma. Preferably, such a preparation should involve the species *Rhodospirillum rubrum* and/or *Phaeospirillum molischianum*.

The invention will now be illustrated by the following examples, which should not be interpreted as limiting the present invention in any way.

EXAMPLES

Example 1

Production of *Rhodospirillum rubrum*

*R. rubrum* strain ATCC 25903 was used for the production of the biomass used in the experiments. Freeze-dried cells were rehydrated in medium R8AH (ATCC medium 550), and cultured in "Segers and Verstraete medium" (see above), using lactic acid (2.7 g/L) as a carbon source, at pH 6.9±0.1. The final culture of the biomass used in the experiments took place in 20 liter-bioreactors, in the same culture medium, at 30±1° C., pH 6.8±0.1, and at constant light intensity (strip light; 300 µM quanta·$m^{-2}$·$s^{-1}$), under anaerobic conditions. After five days of culture, the biomass (3.4 gram wet weight/L) was harvested by continuous centrifugation, stored at −40° C., and freeze-dried.

Example 2

Another Way of Producing *Rhodospirillum rubrum*

To examine the effect of culture conditions on the effectiveness of lowering the cholesterol level, *R. rubrum* ATCC 25903 was also grown anaerobically at 30° C. in 1 liter flasks containing a medium constituted out of 3.1 ml/160% DL-lactate solution, 3 g/l bacteriological peptone and 3 g/l yeast extract in tap water. The pH of the medium was 6.8. The flask were incubated in an incubator (New Brunschwick Scientific, model G 25) on a magnetic stirrer (Variomag multipoint HP15). The flasks were illuminated with an average photon radiation strength of 50 µM quanta·$m^{-2}$·$s^{-1}$, using 3 Tungsten lamps of 40 W. After 3 days of growth, the optical density at 660 nm amounted 3.5 (1.2 g/kg dry weight) and cells were harvested by centrifugation at 6500 g, washed with demineralized water and freeze dried (VirTis freezemobile 24). *R. rubrum* cultured in this way produced the same effect on plasma cholesterol levels as did *R. rubrum* cells cultured as described in Example 1, which were used in most examples.

Example 3

Applicability of Another Strain of *Rhodospirillum rubrum*

Another *R. rubrum* strain, DSM 467, was grown anaerobically at 25° C. in the same way in the same medium as described for Example 2. Cells were harvested after 3 days of growth at an optical density at 660 nm of 4.5 (dry weight 1.4 g/kg) and dried as described for Example 2. Strain DSM 467 produced the same effect on plasma cholesterol levels as did strain ATCC 25903, which was used in most examples.

Example 4

Applicability of the Species *Phaeospirillum molischianum*

Another photosynthetic bacterium, *Phaeospirillum molischianum* DSM 120, was grown in 1 liter flasks with ATCC 550 medium at 25° C. under anaerobic conditions as described for Example 2. Cells were harvested after 3 days of growth at an optical density at 660 nm of 4.0 (dry weight 1.2 g/kg) and dried as described for Example 2.

Example 5

Effect of *R. rubrum* on Chow-Fed Rats

Male Wistar rats were fed a semi-synthetic rat chow, meeting nutritional requirements (as defined in reference 9) (Hope Farms, Woerden, the Netherlands). One group of eight rats was given this basic chow. A second group of eight rats was given the same chow, but now containing in addition 10% (w/w) of freeze-dried *R. rubrum* (in exchange for sucrose). Both groups consumed approximately the same amount of food (31±7 gram/day), and showed the same increase in body weight over time. After eight weeks, all clinical chemistry-parameters measured (plasma glucose, uric acid, urea, creatinine, GOT, GPT, haematocrit, and haemoglobin, and urinary glucose and protein) were similar in both groups, except plasma cholesterol and plasma triglycerides. Plasma cholesterol was significantly lower in the group fed the *R. rubrum*-containing diet (1.2±0.1 mmol/L vs. 1.6±0.1 mmol/L; t-test, p<0.0001), as were plasma triglycerides (0.5±0.1 mmol/L vs. 1.4±0.6 mmol/L; p<0.001) (FIG. 1).

Figure 2:
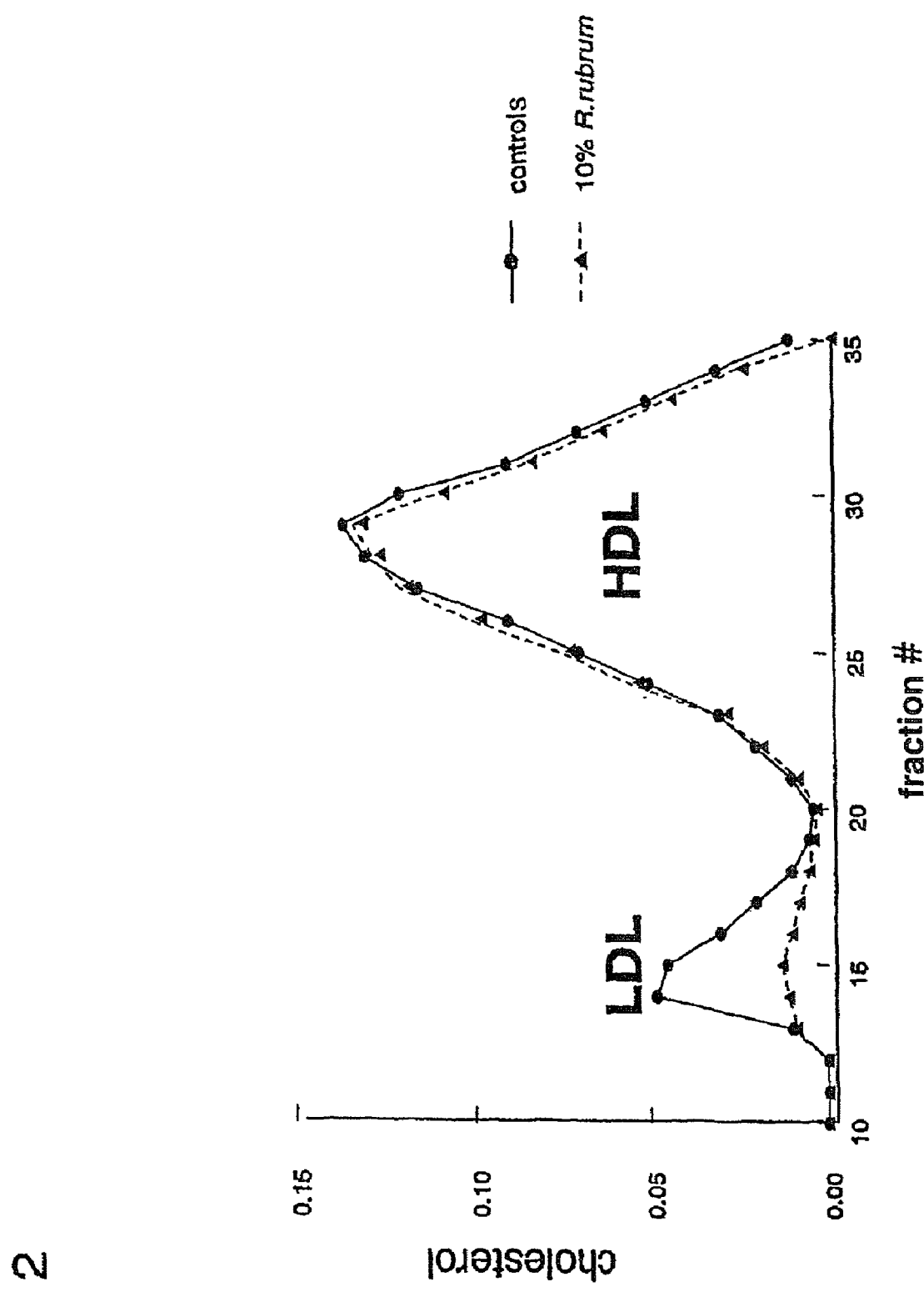
FIG. 2 shows the lipoprotein pattern in plasma from Wistar rats fed a normal chow diet, and from Wistar rats fed a chow diet containing 10% (w/w) *R. rubrum*, as explained in Example 2. (separation by fast protein liquid chromatography).

Separation of the plasma lipoproteins by fast-protein-liquid chromatography (fplc, ÅKTA system of Pharmacia-Amersham) showed that the decrease in cholesterol and triglycerides was due to a decrease of the plasma LDL fraction, while the HDL fraction remained unchanged in the *R. rubrum*-fed animals (FIG. 2). The *R. rubrum*-induced decrease in plasma cholesterol was thus specifically due to a decrease in LDL-cholesterol. Methods used for measuring cholesterol and triglycerides, and for separating lipoproteins by fplc have been described by van Vlijmen et al (1996) and Post et al (2000).

Example 6

The Effect of *R. rubrum* on Chow-Fed Mice

Figure 3:
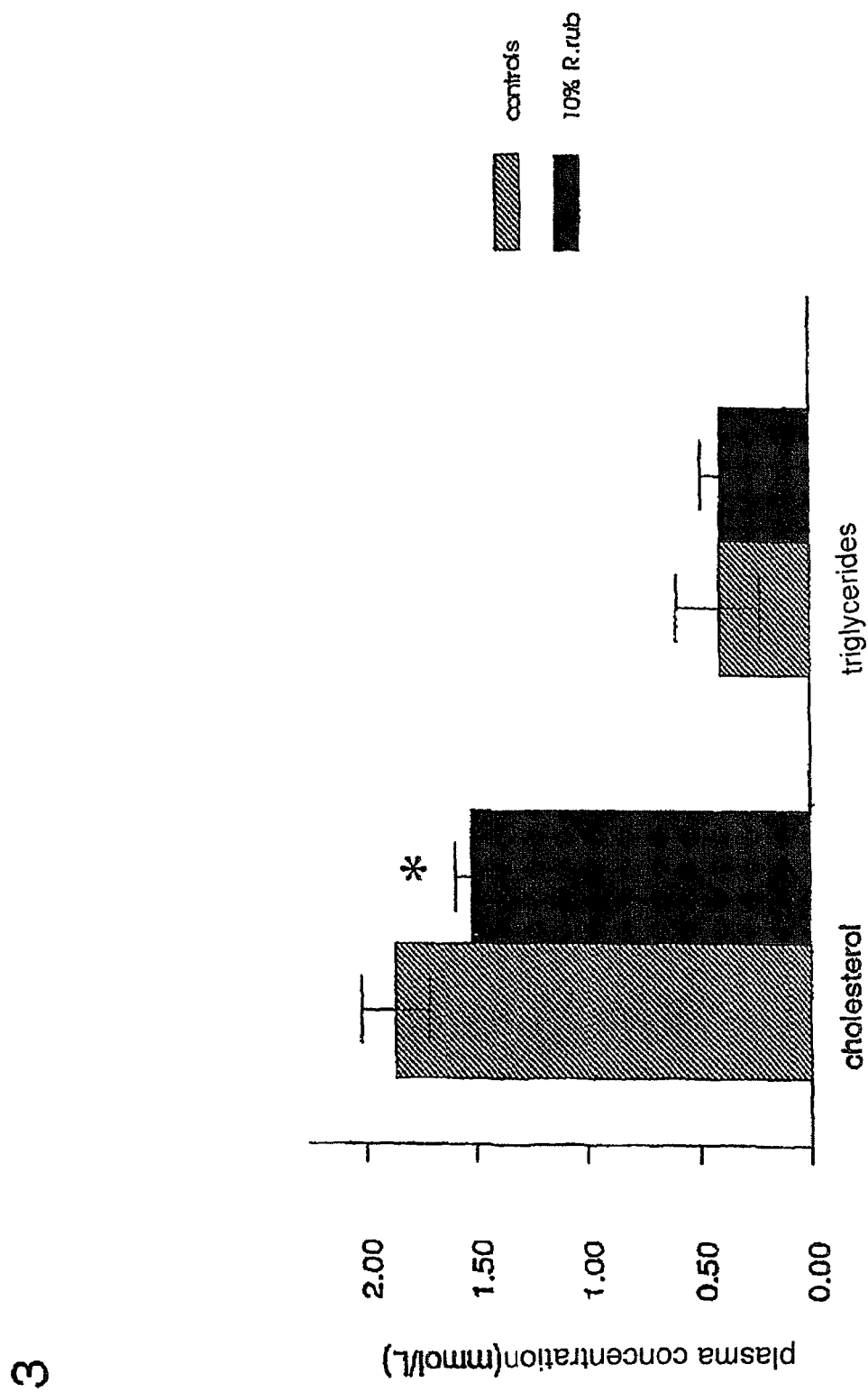
FIG. 3 shows the effect on plasma cholesterol and triglycerides in C57Bl/6 mice fed a normal chow diet, and a chow diet containing 10% (w/w) *R. rubrum*, as explained in Example 3. * means $p<0.003$ relative to controls.

Ten C57Black/6 mice were fed a normal semi-synthetic mouse chow for seven days. Five mice were subsequently given the same chow for another seven days, while the remaining five mice were given for seven days the same mouse chow, but now containing 10% (w/w) of *R. rubrum*. Food intake was not significantly different between groups, and averaged 2.6-2.8 gram/mouse·day. After seven days, the plasma cholesterol level was 1.52±0.07 mmol/L in the *R. rubrum*-fed mice, significantly lower than the plasma cholesterol level in the control group (1.86±0.15 mmol/L; t-test, p=0.003) (FIG. 3). Plasma triglyceride levels were unchanged.

Example 7

Effect of *R. rubrum* in Mice Fed a "Western-Type" Diet

Figure 4:
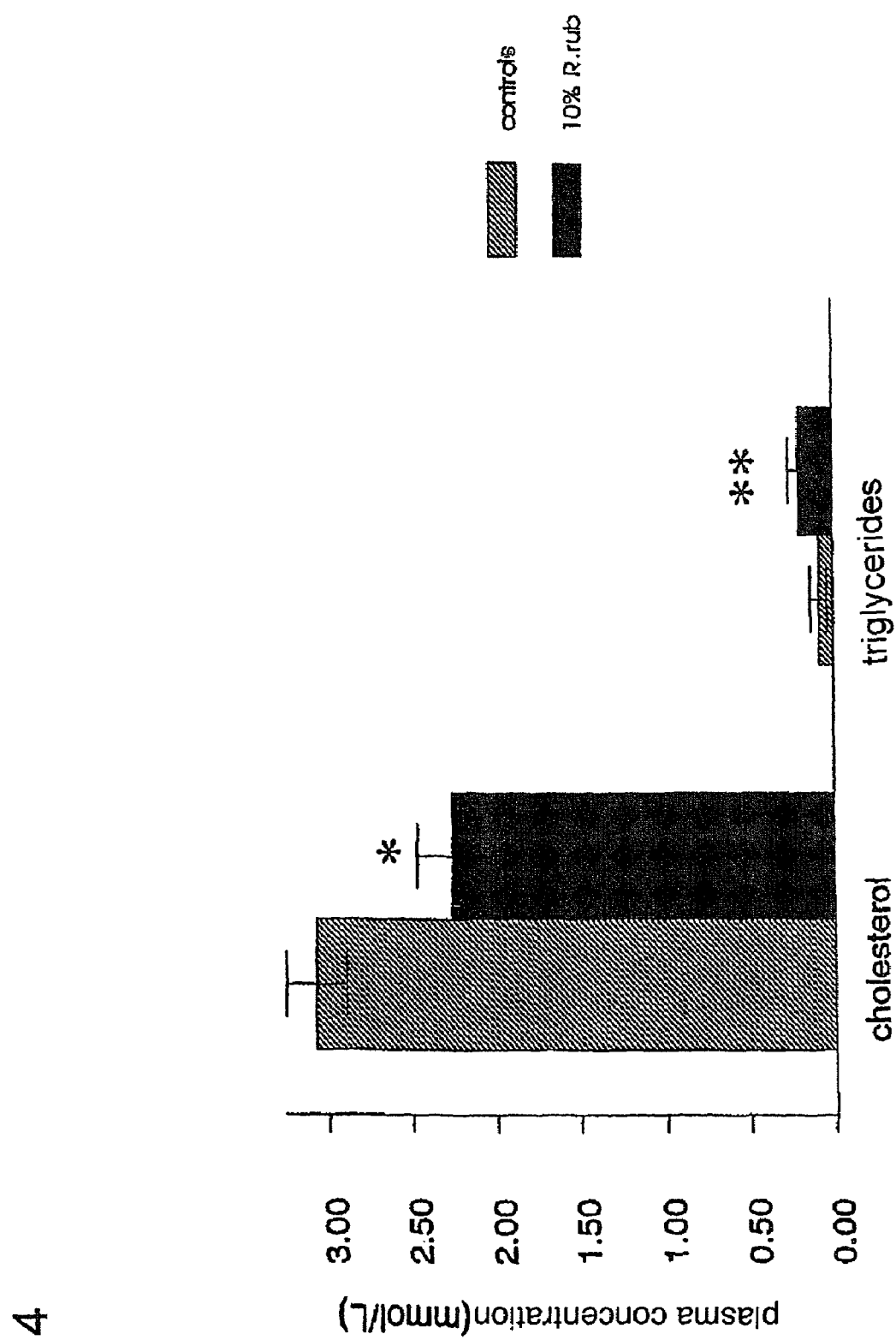
FIG. 4 shows the effect on plasma cholesterol and triglycerides in C57Bl/6 mice fed a hypercholesterolaemic "Western-type" diet, and a hypercholesterolaemic "Western-type" diet containing 10% (w/w) *R. rubrum*, as explained in Example 4. * means $p<0.0003$ relative to controls. ** means $p<0.011$ relative to controls.

Ten C57Black/6 mice were fed for three weeks a semi-synthetic diet, the so-called "Western-type" diet, a diet containing 15% (w/w) fat, and 0.25% (w/w) cholesterol (Nishina et al, 1990). Subsequently, five mice were fed the same diet for seven days, while another five mice were fed the same diet but containing in addition 10% (w/w) *R. rubrum* (some cholesterol was also added to this diet to keep its cholesterol content at 0.25%). After these seven days, the cholesterol level in the control group was 3.07±0.18 mmol/L, while in the group fed the diet containing *R. rubrum* the cholesterol level was 2.26±0.21 mmol/L (t-test, p=0.0003) (FIG. 4). Plasma triglycerides were not decreased.

Figure 5:
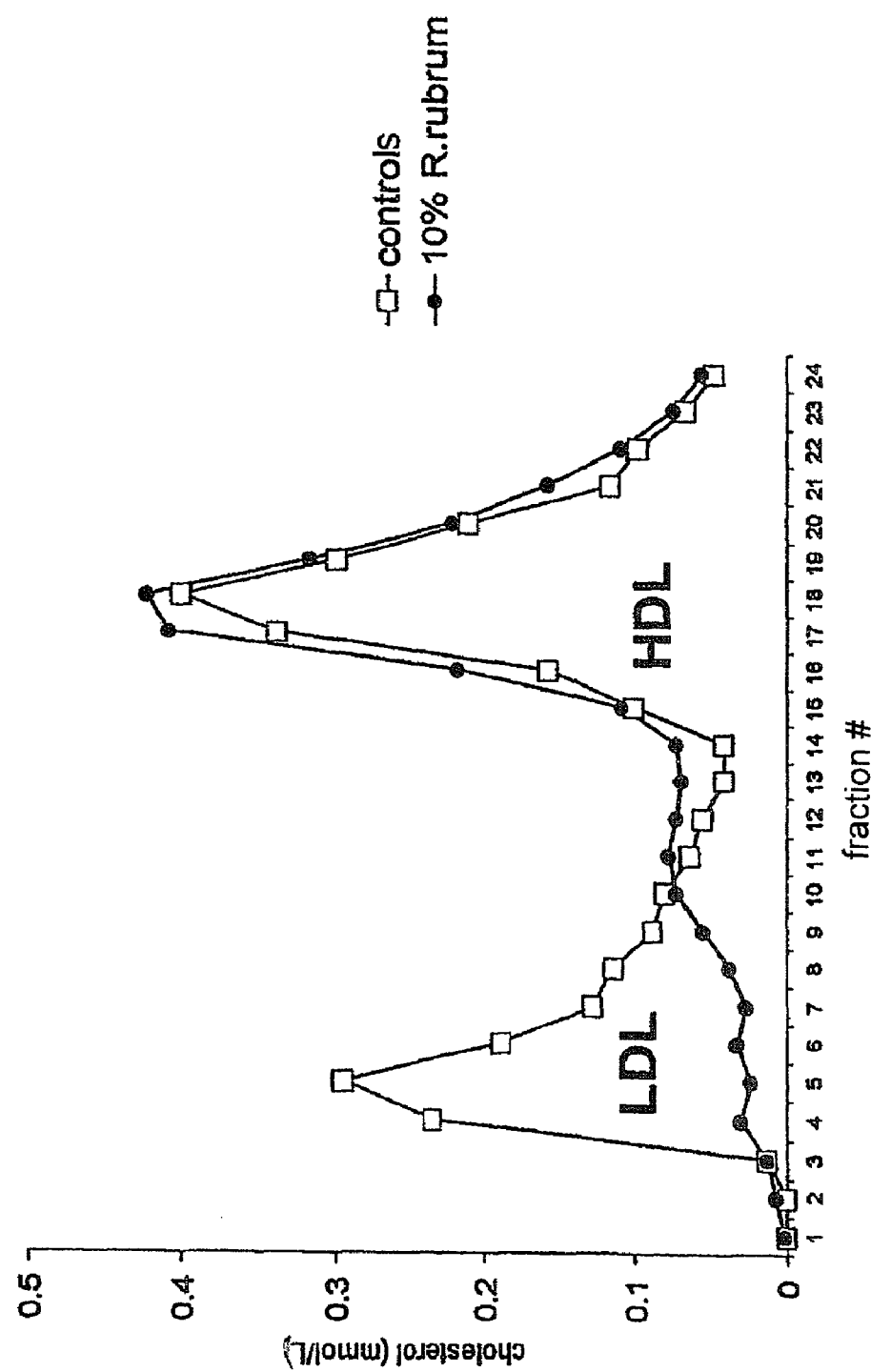
FIG. 5 shows the lipoprotein pattern in plasma from C57Bl/6 mice fed a hypercholesterolaemic "Western-type" diet, and a hypercholesterolaemic "Western-type" diet containing 10% (w/w) *R. rubrum*, as explained in Example 4. (separation by fast protein liquid chromatography).

Separation of the lipoproteins by fplc, showed that the LDL-cholesterol had practically disappeared from the plasma of mice fed the Western-type diet containing *R. rubrum*, while the HDL-cholesterol showed no inter-group difference (FIG. 5).

Example 8

Effect of *R. rubrum* in Transgenic APOE*3Leiden Mice Fed a "Western-Type" Diet

In this experiment mice were used in which the human gene for the so-called Leiden mutation of apolipoprotein E3 (APOE*3Leiden) had been incorporated by transgenesis. Because of this transgenic change, these so-called APOE*Leiden mice have a humanized lipoprotein profile, and are extremely suitable for studying the effect of compounds on lipoprotein metabolism (van Vlijmen et al, 1996; 1998).

The study design was as follows: groups of mice were fed for 5 weeks "Western-type" diet (see above) containing 0.25% (w/w) cholesterol. This diet increased their plasma cholesterol level to 13-14 mmol/L. Subsequently, the mice were randomized, on the basis of their plasma cholesterol level, into groups of six mice each. These groups were given the same diet, but containing in addition 0, 0.625, 1.25, 2.5, 5 or 10% (w/w) freeze-dried *R. rubrum*. The cholesterol content of the diet was kept at 0.25% by adding cholesterol as required.

Figure 6:
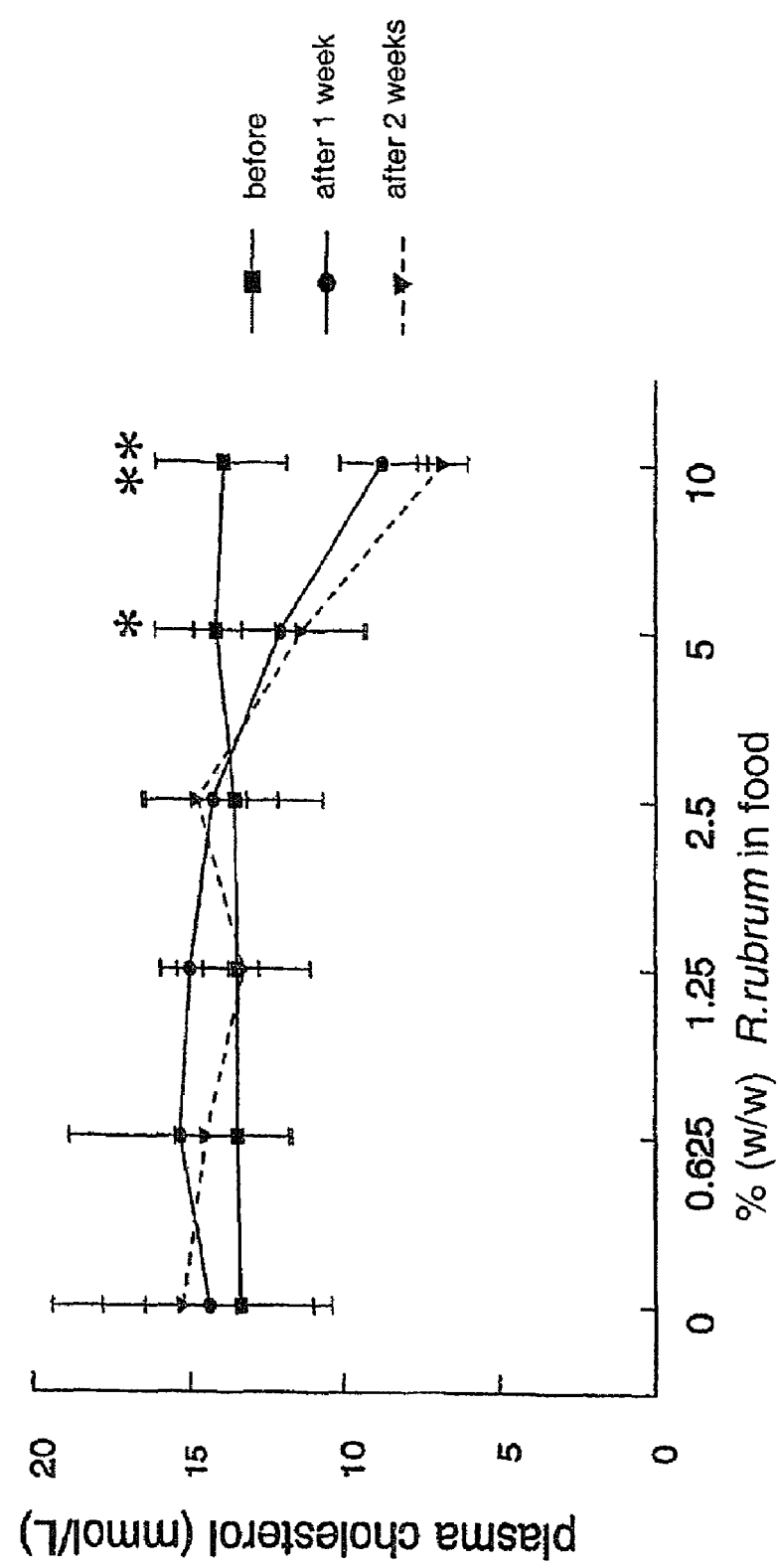
FIG. 6 shows the effect of different concentrations of *R. rubrum* in a "Western-type" diet on plasma cholesterol after one and two weeks, as explained in Example 5. * means significantly different from controls after two weeks ($p<0.001$ relative to controls). ** means significantly different from 0% *R. rubrum* after one week ($p<0.001$ relative to controls) (data shown are mean±s.d.).
Figure 7:
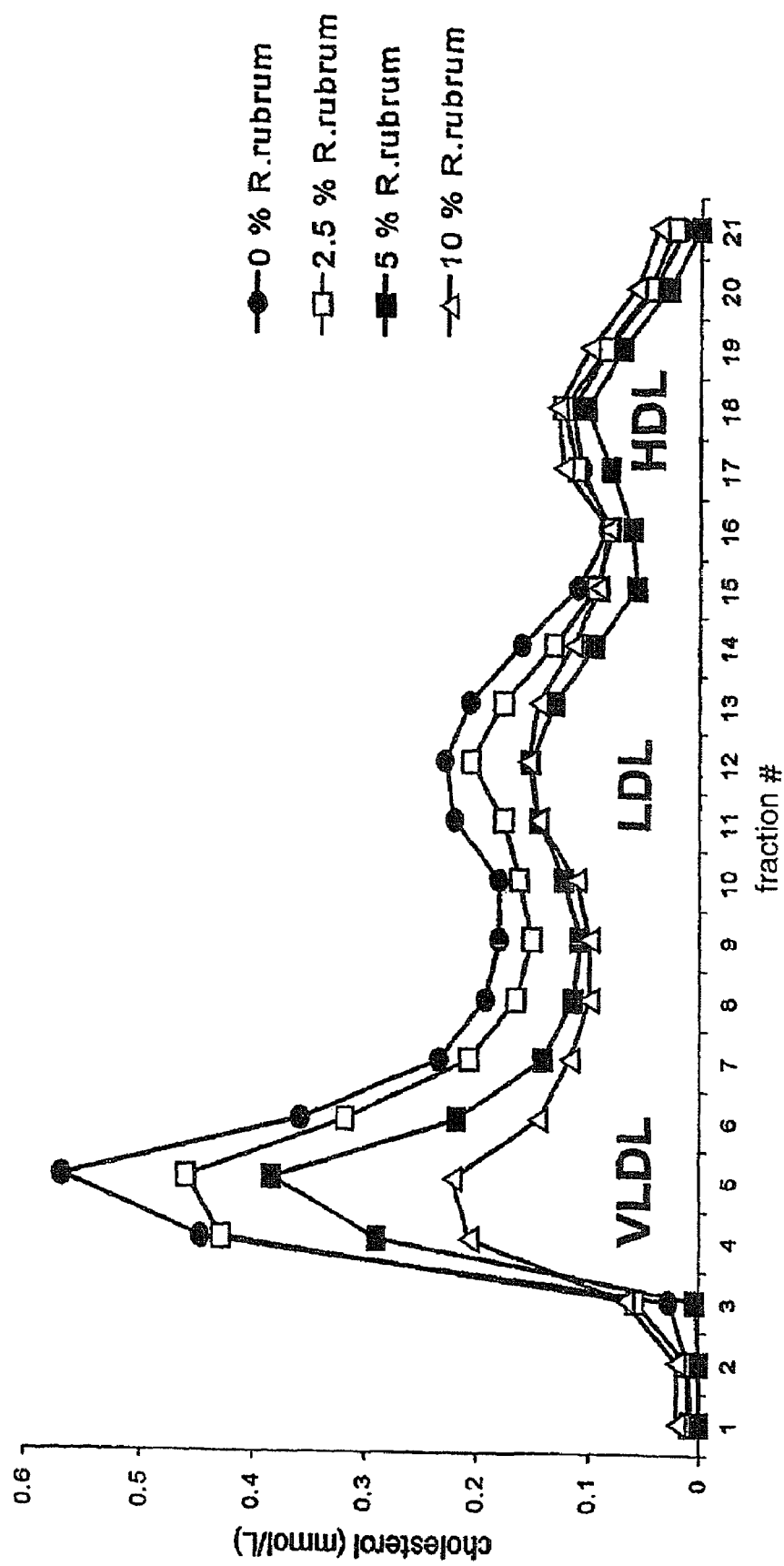
FIG. 7 shows the lipoprotein pattern of APOE3*Leiden mice fed a hypercholesterolaemic "Western-type" diet, and containing different concentrations of *R. rubrum*, as explained in Example 5 (separation by fast protein liquid chromatography).

During the experiment, body weight and food intake were monitored. After the dietary change, blood was taken weekly to determine plasma cholesterol and triglyceride levels. Also, the plasma lipoprotein pattern was determined groupwise in pooled samples by fplc. In addition, faeces were collected weekly on a group basis. After three weeks, VLDL secretion was measured in the groups fed 0% and 10% *R. rubrum* (terminal experiment). The group fed 0.625% *R. rubrum* was then changed to a diet containing 0% *R. rubrum*, the group fed 2.5% *R. rubrum* to 5% *R. rubrum*, and the group fed 5% *R. rubrum* to 10% *R. rubrum*, to replace the two groups sacrificed. After another week, blood was again sampled from the four remaining groups. The results can be summarized as follows:

the plasma cholesterol level was significantly reduced in the groups fed 5% or 10% *R. rubrum* cholesterol lowering was already very significant after one week in the 10% *R. rubrum* group (p<0.0001), and after two weeks also in the 5% *R. rubrum* group (p<0.001), and remained so for the three-week period (FIG. 6)

this lower cholesterol level was due to a lowering of cholesterol in the VLDL and LDL fractions, while the amount of cholesterol in the HDL fractions did not change (FIG. 7)

Figure 8:
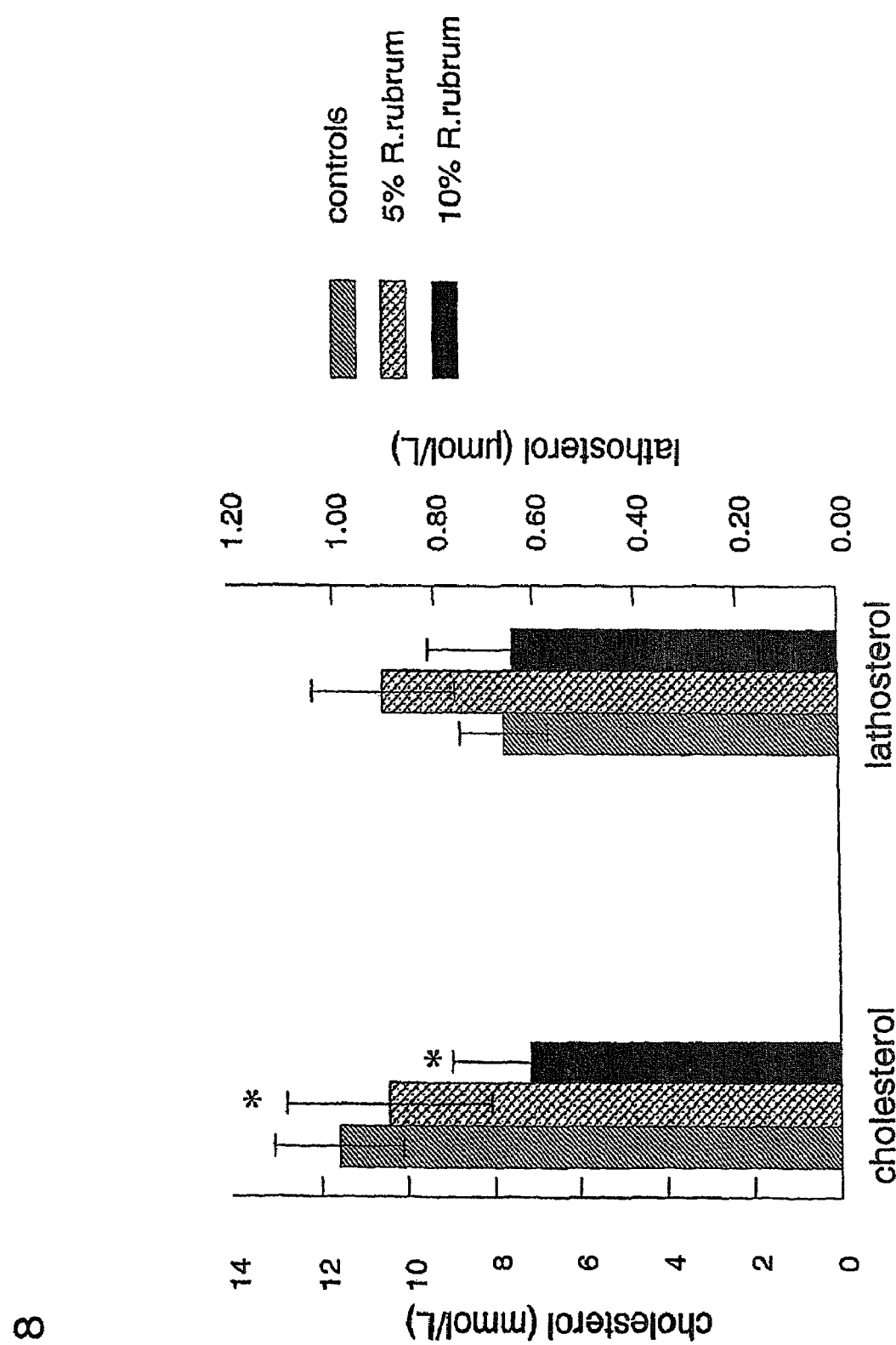
FIG. 8 shows the effect of different concentrations of *R. rubrum* in a "Western-type" diet on plasma cholesterol and lathosterol after two weeks, as explained in Example 5. * means significantly different from controls (data shown are mean±s.d.).

To decide whether the cholesterol lowering was due to inhibition of cholesterol synthesis, the plasma concentration of lathosterol, a side product of the cholesterol synthesis pathway, was measured (Kempen et al, 1988). The plasma lathosterol level was not significantly different between the groups fed 0, 5 or 10% *R. rubrum*; while, as mentioned above, the plasma cholesterol level was significantly lower in the 5% and 10% groups (FIG. 8). The ratio of plasma lathosterol to plasma cholesterol even increased significantly in the mice fed *R. rubrum* (ANOVA<p<0.026). Since the (relative) lathosterol concentration is a good reflection of the rate of cholesterol synthesis (Kempen et al, 1988), it can be concluded that the lowering of plasma cholesterol in the 5% and 10% *R. rubrum*-fed groups was not due to a decreased rate of cholesterol synthesis.

Figure 9:
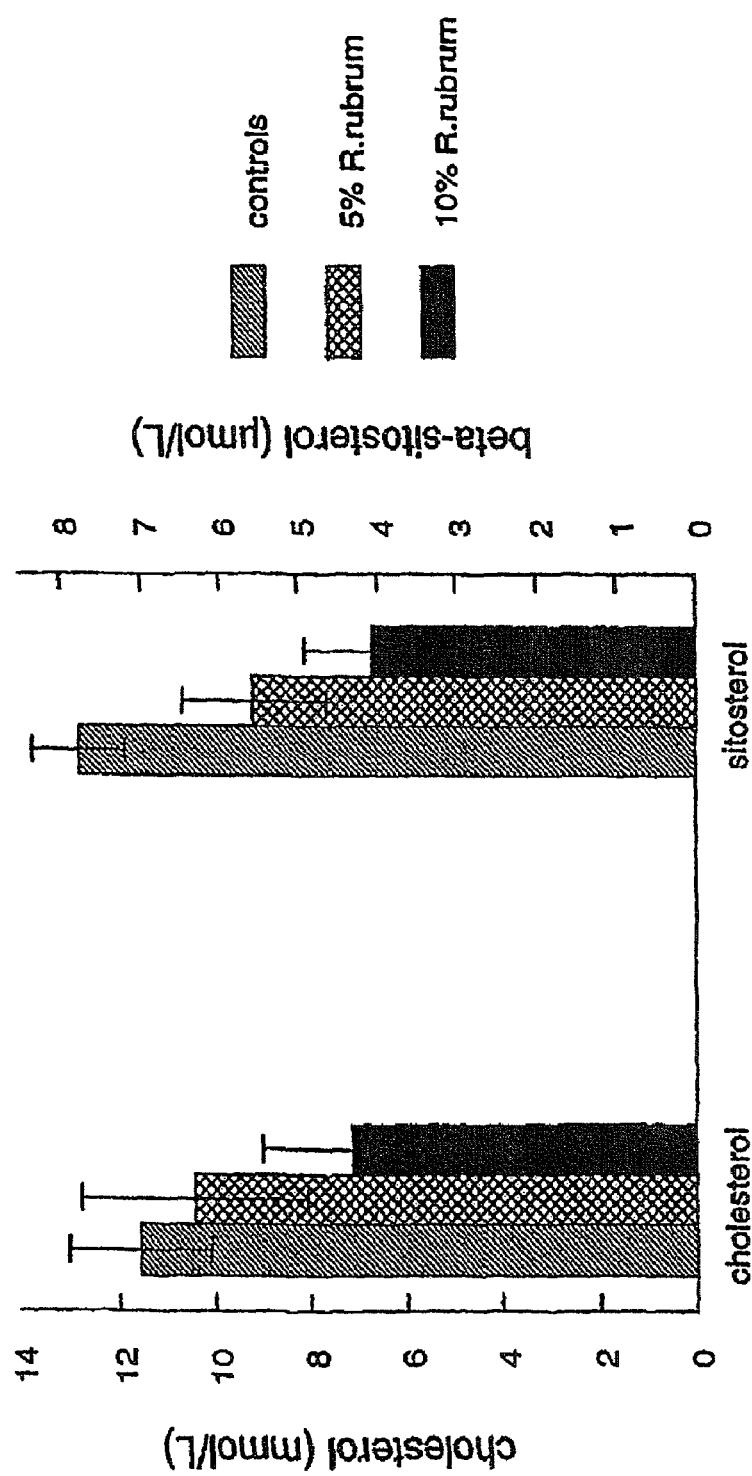
FIG. 9 shows the effect of different concentrations of *R. rubrum* in a "Western-type" diet on plasma cholesterol and β-sitosterol after two weeks, as explained in Example 5 (data shown are mean±s.d.).

The plasma levels of camposterol and β-sitosterol, two sterols that occur only in plants and can thus only be present in plasma after uptake from the intestines, decreased significantly in the groups fed either 5% or 10% *R. rubrum* (FIG. 9). The ratio of the plasma concentration of β-sitosterol to cholesterol did not change significantly (ANOVA, p=0.26), however; neither did the ratio of plasma camposterol to cholesterol. (ANOVA, p=0.98). Since the plasma concentration of cholesterol is determined by its rate of synthesis and its rate of absorption from the intestines, the fact that these ratios remained similar (camposterol, β-sitosterol; compare Miettinen et al, 1990) or increased (lathosterol) demonstrates that the decrease in the plasma cholesterol concentration cannot be due to a decrease in cholesterol synthesis, but must rather be ascribed to an decreased absorption of sterols from the intestinal lumen.

Figure 10:
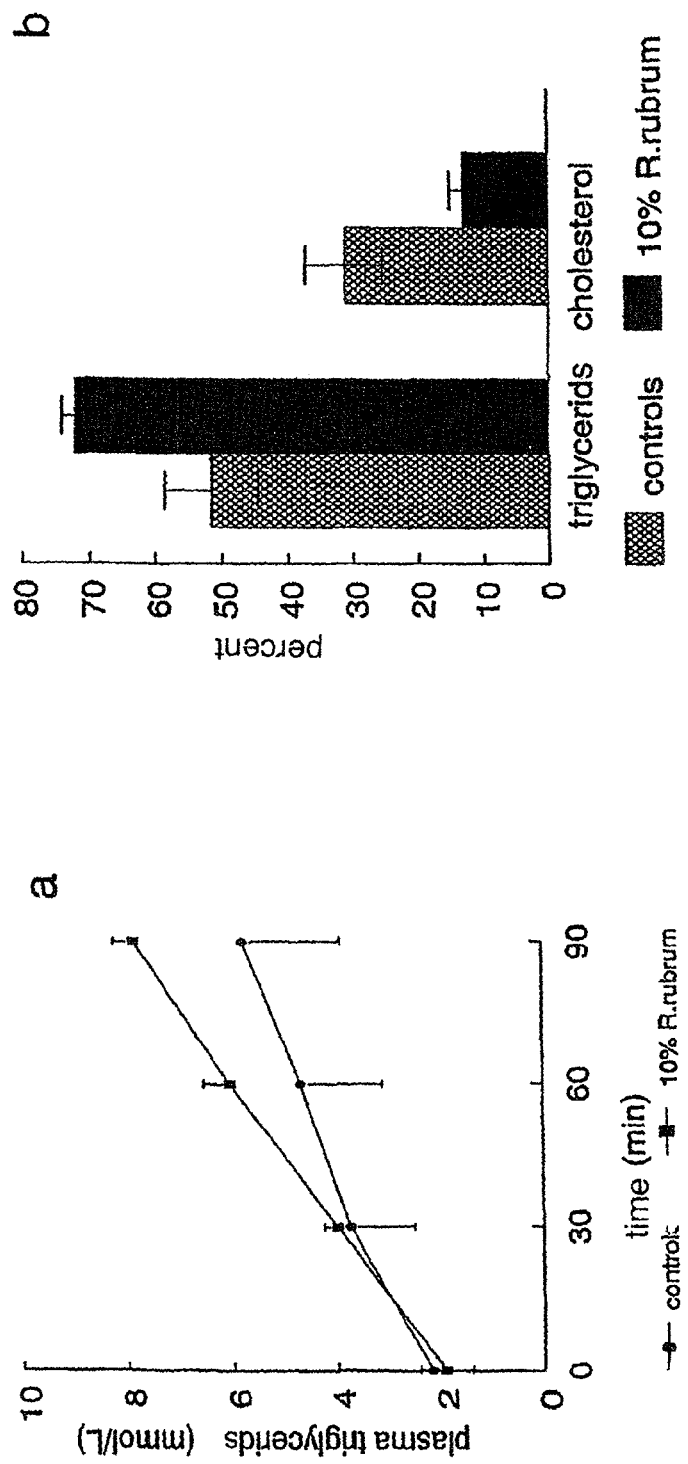
FIG. 10 shows the synthesis of VLDL-triglycerides (frame a) and the lipid composition of VLDL (frame b) in mice fed a "Western-type" diet containing different concentrations of *R. rubrum*, as explained in Example 5.

The synthesis of VLDL by the liver (measured as described by Post et al, 2000) was not significantly different in the group fed 10% *R. rubrum*, relative to the control group (FIGS. 10a,b). Although, after the injection of Triton WR1339, plasma triglyceride concentrations increased more rapidly in the group fed 10% *R. rubrum* than in the control group (FIG. 10a), this should be ascribed to the higher amount of triglycerides in the VLDL fraction of *R. rubrum*-fed mice (FIG. 10b), rather than to an increase in the secretion of VLDL particles by the liver.

Figure 11:
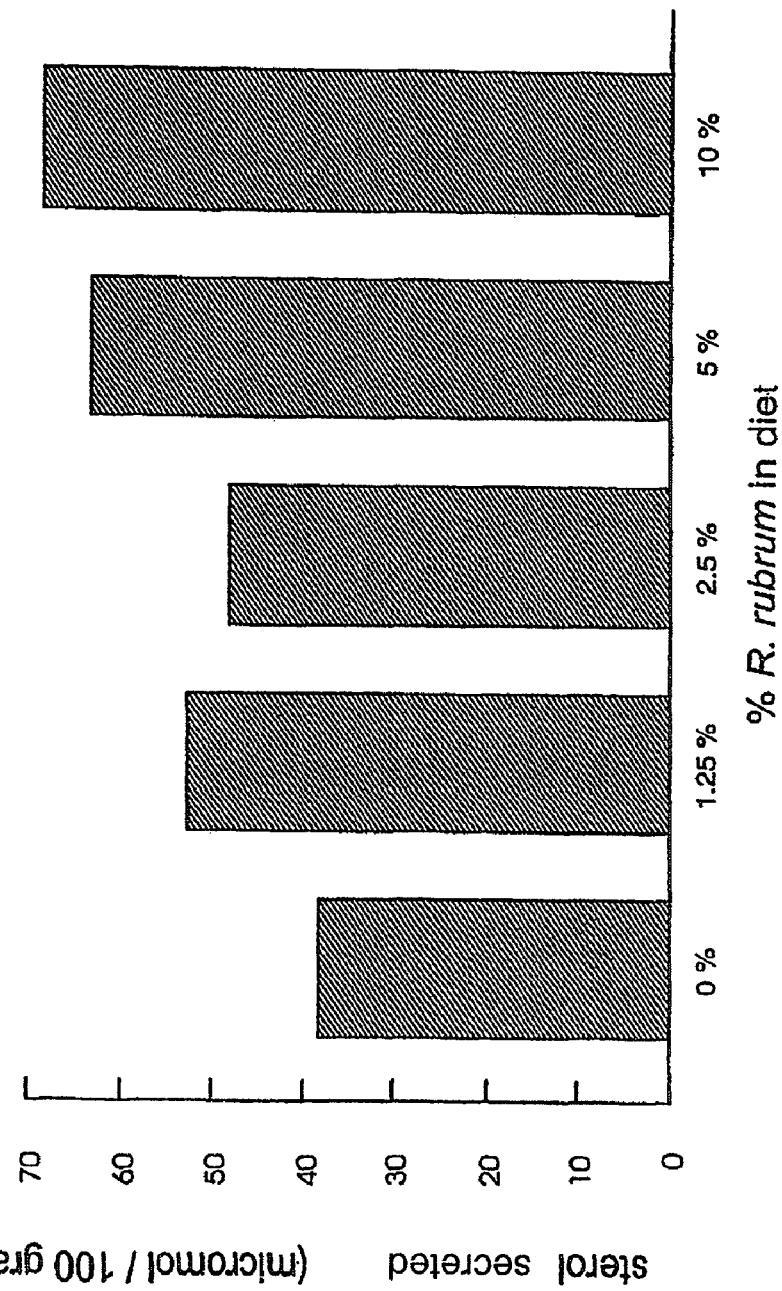
FIG. 11 shows the excretion of neutral sterols in faeces of mice fed a "Western-type" diet containing different concentrations of *R. rubrum*, as explained in Example 5.
Figure 12:
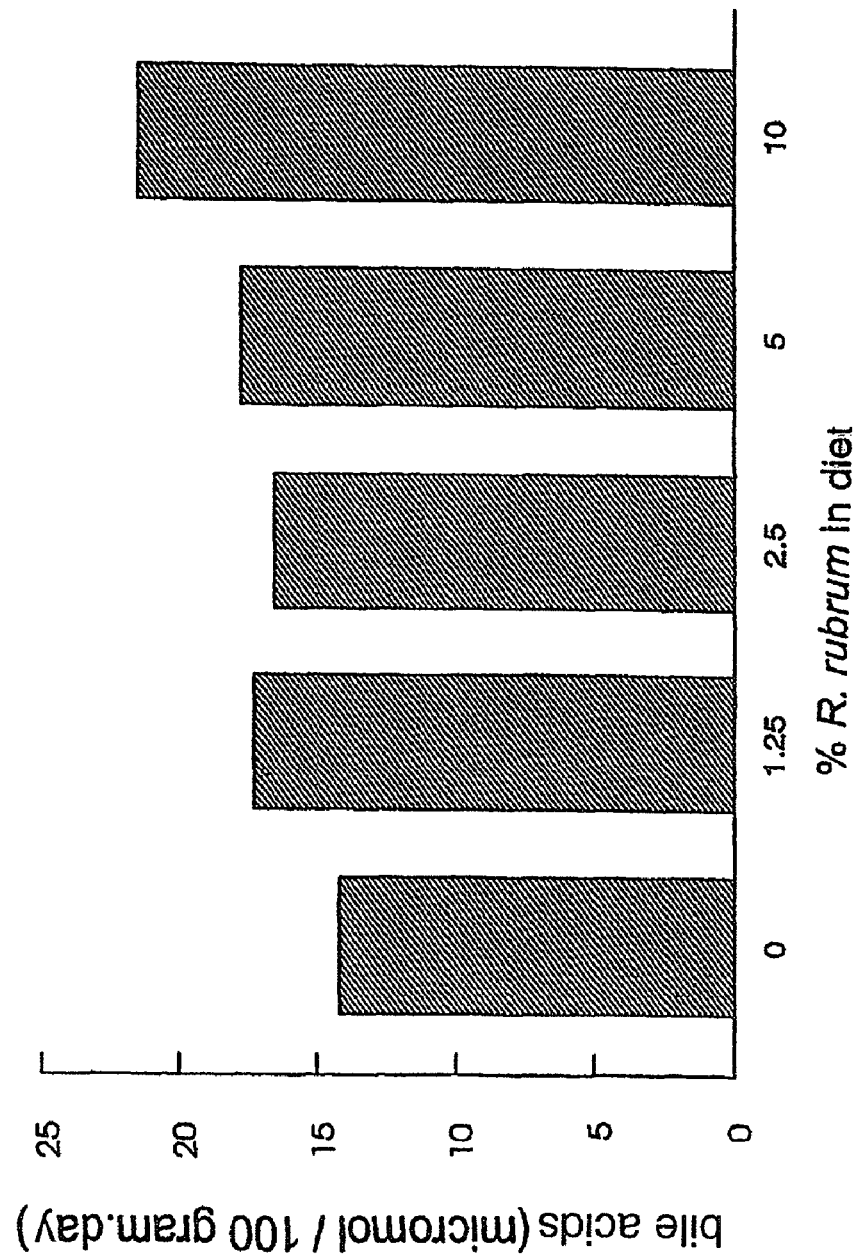
FIG. 12 shows the excretion of bile acids in faeces of mice fed a "Western-type" diet containing different concentrations of *R. rubrum*, as explained in Example 5.
Figure 13:
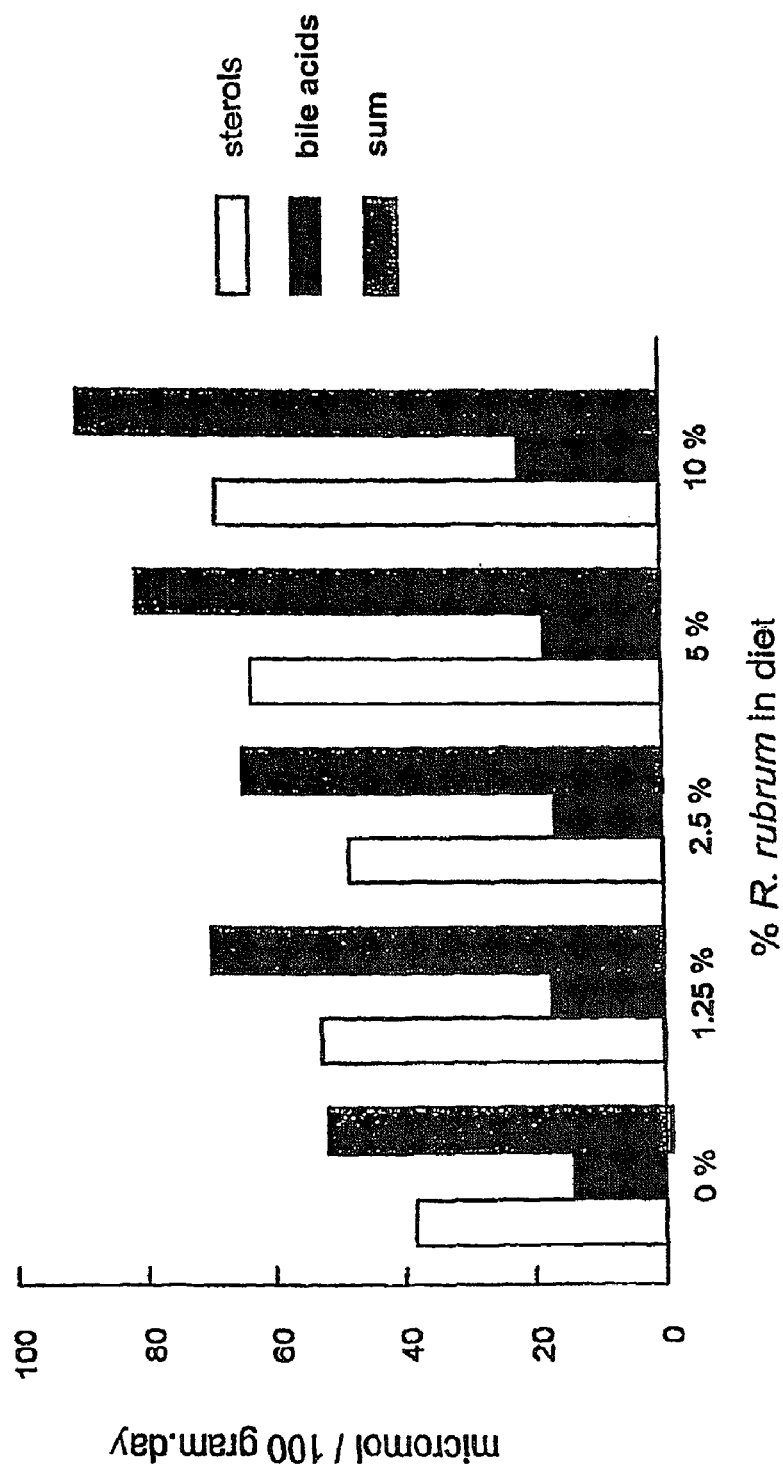
FIG. 13 shows the excretion of neutral sterols plus bile acids in faeces of mice fed a "Western-type" diet containing different concentrations of *R. rubrum*, as explained in Example 5.

The faecal excretion of neutral sterols (especially cholesterol) increased in the mice treated with *R. rubrum* (FIG. 11), while the faecal excretion of bile acids also increased slightly (FIG. 12). Consequently, the faecal excretion of all sterols jointly (neutral sterols plus bile acids) increased (FIG. 13) (see also text Tables 1a and b).

Example 9

Effect of a Membrane Fraction of *Rhodospirillum rubrum* on Plasma Cholesterol Level in APOE*3Leiden Mice Five gram of freeze-dried *R. rubrum* was suspended in 25 ml of water, and sonicated in a Branson Sonifier B-12 for one minute at full strength. The sonicate was then centrifuged at 21,000 rpm, and the supernatant and pellet were separated. The pellet was resuspended and recentrifuged. Pellet and supernatant were separately mixed into the W-diet (described above) containing 0.25% cholesterol to 10% (w/w), assuming both pellet and supernatant to be equivalent to 5 gram of freeze-dried *R. rubrum* (i.e., the starting material). Groups of six APOE3*Leiden mice were fed diet W, or the diet W but also containing the pellet (membraneous) material, or the diet W but also containing the cytoplasmic material, for two weeks. At week 2, plasma cholesterol was 15.7±1.6 mmol/L in the mice fed the control diet W, in the mice fed the diet W also containing the cytoplasmic material, plasma cholesterol was 14.4±2.1 mmol/L, while in the mice fed the diet W also containing the membraneous material, the plasma cholesterol was 6.7±0.9 mmol/L, a significant reduction of 57% relative to the control group (t-test; p<0.001).

Example 10

Effect of *Phaeospirillum molischianum* on Plasma Cholesterol Level in APOE*3Leiden Mice Eleven APOE*3Leiden mice were fed the "Western-type" diet (see above) containing 0.25% (w/w) cholesterol. This diet increased their plasma cholesterol level to 9±3 mmol/L. Subsequently, the mice were randomized, on the basis of their plasma cholesterol level, into groups of six mice each. The two groups were given the same diet, but containing in addition 0 or 10% (w/w) freeze-dried *Phaeospirillum molischianum*, as described above for *R. rubrum*. After ten days of feeding, plasma cholesterol averaged 10±4 mmol/L in the group not given *P. molischianum* (paired t-test: not significant), and 5±2 mmol/L in the group given 10% *P. molischianum* in the feed (paired t-test: p<0.05).

In Summary:

These experiments show that adding 5% (w/w) or 10% (w/w) of *R. rubrum* to a "Western-type" diet reduces, in APOE*3Leiden mice, plasma cholesterol levels significantly. This decrease 1. can fully be ascribed to a decrease of cholesterol carried in (pro-atherogenic) VLDL and LDL particles, while (anti-atherogenic) HDL cholesterol remains unchanged;
2. is not caused by a decrease in cholesterol synthesis, since plasma lathosterol levels do not change, while the synthesis/secretion of VLDL by the liver is also unchanged;
3. is not due to an increased excretion of bile acids, which is only slightly increased; but
4. is therefore most likely due to a decreased absorption of sterols from the intestines, as reflected by the increased excretion of cholesterol in the faeces (see Text Table 1a), and the decrease in plasma camposterol and β-sitosterol concentrations.
5. is caused by membraneous cellular material, not by soluble cytoplasmatic cellular material.

The cholesterol-lowering effect is caused by *R. rubrum* cultured under different conditions, is caused by at least two different strains of *R. rubrum* (ATCC 25903 and DSM 467), and is also caused by a related species, *P. mnolischianum*.

TEXT TABLE 1a

Sterol balance in APOE*3Leiden mice fed "Western-type" diet, containing 0.25% (w/w) cholesterol and varying amounts of *R. rubrum*

| Concentration of *R. rubrum* in the diet (% w/w) | INPUT cholesterol in the food eaten (a) | OUTPUT sterols excreted in faeces (b) | OUTPUT bile acids excreted in faeces | OUTPUT total excreted in faeces |
|---|---|---|---|---|
| 0 | 78 | 38 | 14 | 52 |
| 0.625 | 78 | 41 | 18 | 59 |
| 1.25 | 78 | 52 | 17 | 69 |
| 2.5 | 78 | 48 | 15 | 63 |
| 5 | 78 | 63 | 17 | 80 |
| 10 | 78 | 68 | 25 | 93 |

All data are expressed as µmoles per 100 gram mouse per day

TEXT TABLE 1b

Intestinal cholesterol absorption in APOE*3Leiden mice fed "Western-type" diet, containing 0.25% (w/w) cholesterol and varying amounts of *R. rubrum*

| Concentration of *R. rubrum* in the diet (% w/w) | Cholesterol absorbed (µmoles per 100 gram body weight per day) [(a) minus (b)] | Cholesterol absorbed (as % of input) | Cholesterol absorbed (as % of control group) |
|---|---|---|---|
| 0 | 40 | 51 | 100 |
| 0.625 | 37 | 48 | 93 |
| 1.25 | 26 | 33 | 64 |
| 2.5 | 30 | 38 | 75 |
| 5 | 15 | 19 | 37 |
| 10 | 10 | 12 | 24 |

(a) and (b) refer to Text Table 1a.

REFERENCES

1. Deutsche Sammlung von Mikroorganismen und Zellkulturen GmbH. Bacterial nomenclature up-to-date. Accessed Dec. 6, 2003. www.dsmz.de/bactnom/bactname.htm.
2. Euzéby J P. List of bacterial names with standing in nomenclature. Accessed Dec. 6, 2003. www.bacterio.cict.fr/qr/rhodospirillum.html and www.bacterio.cict.fr/qr/phaeospirillum.html.
3. Hassel C A. Animal models: new cholesterol raising and lowering nutrients. Curr Opin Lipidol 1998; 9:7-10.
4. Imhoff J F, Trüper H G. The genus *Rhodospirillum* and related genera. Chapter 101 in: Balows A, Trüper H G, Dworkin M, Harder W, Schleifer K-H. The Prokaryotes. A Handbook on the Biology of Bacteria: Ecophysiology, Isolation, Identification, Applications. Springer-Verlag, New York/Berlin/Heidelberg, Volume III, $2^{nd}$ edition 1992, pp. 2141-2155.
5. Imhoff J F, Petri R, Suling J. Reclassification of species of the spiral-shaped phototrophic non-sulfur bacteria of the alpha-Proteobacteria: description of the new genera *Phaeospirillum* gen.nov., *Rhodovibrio* gen.nov., *Rhodothalassium* gen.nov. and *Roseospira* gen.nov. as well as transfer of *Rhodospirillum fulvum* to *Phaeospirillum fulvum* comb.nov., of *Rhodospirillum molischianum* to *Phaeospirillum molischianum* comb.nov., of *Rhodospirillum salinarum* to *Rhodovibrio salexigens*. Int J System Bacteriol 1998; 48: 793-798.
6. Kempen H J, Glatz J F, Gevers Leuven J A, van der Voort H A, Katan M B. Serum lathosterol concentration is an indicator of whole-body cholesterol synthesis in humans. J Lipid Res 1988; 29: 1149-1155.
7. Miettinen T A, Tilvis R S, Kesäniemi Y A. Serum plant sterols and cholesterol precursors reflect cholesterol absorption and synthesis in volunteers of a randomly selected male population. Am J Epidemiol 1990; 131: 20-31.
8. Nishina P M, Verstuyft J, Paigen B. Synthetic low and high fat diets for the study of atherosclerosis in the mouse. J Lipid Res 1990; 31: 859-869.
9. Nutrient Requirements of Laboratory Animals. National Academy of Sciences publication #10, 3rd revised edition. Washington D.C., 1978.
10. Post S M, de Roos B, Vermeulen M, Afman L, Jong M C, Dahlmans V E H, Havekes L M, Stellaard F, Katan M B, Princen H M G. Cafestol increases serum cholesterol levels in apolipoprotein E*3-Leiden transgenic mice by suppression of bile acid synthesis. Arterioscler Thromb Vasc Biol 2000, 20: 1551-1556.

11. Segers L, Verstraete W. Conversion of organic acids to H2 by Rhodospirillaceae grown with glutamate or dinitrogen as nitrogen source. Biotechnol Bioeng 1983; 25: 283-2853.
12. Van Vlijmen B J M, van 't H of H B, Mol M J T M, van der Boom H, van der Zee A, Frants R R, Hofker M H, Havekes L M. Modulation of very low density lipoprotein production and clearance contributes to age and gender-dependent hyperlipoproteinaemia in apolipoprotein E3-Leiden transgenic mice. J Clin Invest 1996; 97: 1184-1192.
13. Van Vlijmen B J, Pearce N J, Bergo M, Staels B, Yates J W, Gribble A D, Bond B C, Hofker M H, Havekes L M, Groot P H. Apolipoprotein E*3-Leiden transgenic mice as a test model for hypolipidaemic drugs. Arzneimittelforschung 1998; 48:396-402.

The invention claimed is:

1. A method for lowering plasma cholesterol level in a subject comprising administering to the subject a preparation comprising an isolated membrane fraction separated from cytoplasmic material, the membrane fraction made from bacteria of *Rhodospirillum* spp. and/or *Phaeospirillum* spp.

2. The method of claim 1, wherein the subject is human.
3. The method of claim 1, wherein the preparation comprises one or more excipients.
4. The method of claim 1, wherein the preparation is a foodstuff, a probiotic composition, or a food supplement.
5. The method of claim 1, wherein the bacteria are of the species *Rhodospirillum rhubrum*.
6. The method of claim 5, wherein the bacteria are of the strain ATCC 11170 or of the strain ATCC 25903.
7. The method of claim 1, wherein the bacteria are of the species *Phaeospirillum molischianum*.
8. The method of claim 7, wherein the bacteria are of the strain DSM 120.
9. The method of claim 1, wherein the preparation comprises 20-100 w/w % of bacterial membranous material.
10. A method for lowering plasma cholesterol level in a subject comprising:
    (a) producing a preparation comprising an isolated membrane fraction separated from cytoplasmic material, the membrane fraction made from bacteria of *Rhodospirillum* spp. and/or *Phaeospirillum* spp.; and
    (b) administering the preparation to the subject.

* * * * *

UNITED STATES PATENT AND TRADEMARK OFFICE
CERTIFICATE OF CORRECTION

| | | |
|---|---|---|
| PATENT NO. | : 7,749,513 B2 | |
| APPLICATION NO. | : 12/368583 | |
| DATED | : July 6, 2010 | |
| INVENTOR(S) | : Josephus Jan Emeis et al. | |

It is certified that error appears in the above-identified patent and that said Letters Patent is hereby corrected as shown below:

Column 1, lines 5-11, delete and replace with, --This is a divisional application of U.S. Application No. 10/538,531, (abandoned), filed on June 10, 2005 as a 371 national phase filing of PCT/NL2003/000884, which was filed on December 12, 2003 claiming priority to Dutch Application No. NL 1022153, filed December 12, 2002. Each of the above named related applications is incorporated herein by reference. --;

Column 13, line 45, "P. mnolischianum" should read --P. molischianum--; and

Column 16, line 7, "rhubrum" should read --rubrum--.

Signed and Sealed this
Ninth Day of August, 2011

David J. Kappos
*Director of the United States Patent and Trademark Office*